United States Patent [19]
O'Shea

[11] Patent Number: 6,149,275
[45] Date of Patent: Nov. 21, 2000

[54] APPARATUS FOR SELECTION OF AN OPTICAL LENS

[75] Inventor: Donald W. O'Shea, Lakewood, Ohio

[73] Assignee: Mack Products Co., Lakewood, Ohio

[21] Appl. No.: 09/204,889

[22] Filed: Dec. 3, 1998

[51] Int. Cl.⁷ ........................................... A61B 3/02
[52] U.S. Cl. ................................................ 351/233
[58] Field of Search ................................ 351/216, 217, 351/218, 233, 234, 235, 236, 213, 246

[56] References Cited

U.S. PATENT DOCUMENTS

| | | |
|---|---|---|
| 4,027,954 | 6/1977 | Good . |
| 4,452,515 | 6/1984 | Lewis . |
| 4,740,072 | 4/1988 | Griffin et al. . |
| 5,223,864 | 6/1993 | Twisslman ............................... 351/233 |
| 5,650,839 | 7/1997 | Sims ........................................ 351/218 |

*Primary Examiner*—George Manuel
*Attorney, Agent, or Firm*—Oldham & Oldham Co., LPA

[57] ABSTRACT

An optical lens selection apparatus by which an individual who engages in an activity such as welding, machining, wood working or the like, and who wishes to obtain enhanced viewing of a work piece may readily choose an appropriate lens for use with a protective eye mask. The apparatus of the present invention is comprised generally of: a box-like casing; a lens evaluation compartment fixed to the casing; a drum member situated within and movably attached to the lens evaluation compartment; a plurality of slide-like plates, each of the slide-like plates being provided with an optical lens, the plurality of slide-like plates being fixed to the drum member; and a viewing means releasably attachable to the lens evaluation compartment for use with the drum member and the plurality of optical lenses fixed thereto. A user of the apparatus may evaluate the optical lenses to find the most suitable of them by rotating each lens into alignment with the rectangular opening and viewing the rear wall of the casing compartment and then selecting the desired lens for insertion into a eye mask from any one of a number of lens storage compartments provided on the front panel of the apparatus.

20 Claims, 3 Drawing Sheets

APPARATUS FOR SELECTION OF AN OPTICAL LENS

FIELD OF THE INVENTION

The present invention relates to an optical lens selection apparatus by which an individual who engages in an activity such as welding and who wishes to obtain enhanced viewing of a work piece to be welded may readily choose an appropriate lens for use with a protective eye mask.

BACKGROUND OF THE INVENTION

Protective eye masks have long been known for use in a wide variety of activities including, but not limited to, welding, machining, and wood working. Oftentimes, such activities can best be carried out if the equipment operator has not only the necessary eye protection against the potential injury causing aspects of the task, but also a close-up view of the object or objects upon which work is to be undertaken. In the case of welding, a welder may be able to produce a higher quality weld if, during the welding process, the welder has a close range view of a joint at which two or more components are to be welded together. Similarly, a machinist may be able to provide a better machined article by having an enlarged view of the blank to be turned during the machining process. In these and other instances, better visional definition obtained by the operator can result in better visual control over the process, and better control can in turn account for better end results.

In order to achieve the aforedescribed visual capabilities, protective eye masks have been outfitted with optical lenses, frequently embodied in the form of slide-like plates, which can be used either alone or in conjunction with other see-through barriers making up a typical protective eye mask. A conventional technique for determining which one of a number of optical lenses is best suited to provide the required amount of visual acuity for any particular individual involves traditional techniques of vision analysis, which are frequently carried out at a location away from the lens usage site and which very often do not allow for immediate delivery of the lens found to be appropriate. Examples of known devices employed to perform traditional analytical techniques are provided in U.S. Pat. Nos. 4,740,072; 4,452,515 and 4,027,954.

The availability of a simple, low cost apparatus for selecting an optical lens for a protective eye mask, which can be quickly and easily operated by the individual mask wearer at or near the point of mask use and which contains a readily available, immediately usable supply of lenses will have considerable appeal.

SUMMARY OF THE INVENTION

The apparatus of the present invention is comprised generally of: a box-like casing; a lens evaluation compartment fixed to the casing; a drum member situated within and movably attached to the lens evaluation compartment; a plurality of slide-like plates, each of the slide-like plates being provided with an optical lens, the plurality of slide-like plates being fixed to the drum member; and a viewing means releasably attachable to the lens evaluation compartment for use with the drum member and the plurality of optical lenses fixed thereto. The box-like casing, which may be fabricated of any sturdy material, includes a horizontal base, a front panel, a rear panel, a left side panel, a right side panel and an interior dividing panel. The lens evaluation compartment is an elongated, open-backed enclosure having a bottom member, a top member, a left side member, a right side member and a front member having a rectangular opening. The lens evaluation compartment has a length, height and depth that permits its bottom member to be fixed to a horizontal shelf member formed by an upper portion of the front panel of the box-like casing. The drum member, which is hollow and is shaped like a multi-faceted prism, includes two drum ends and a plurality of drum sides that extend between the drum ends. The drum ends have rotatable fastening means that extend through the left and right side members of the lens evaluation compartment and that engage knob-like rotating means use to turn the drum member in the lens evaluation compartment. Each of the drum sides is comprised of a frame-like holding means that is transversely separated by a dividing member into left and right portions. Each frame-like holding means is dimensionally the same, with regard to its length and width, as the opening provided in the front member of the lens evaluation compartment. Each left and right portion of the holding means securely contains one of the slide-like plates, which is provided with an optical lens. The drum member is positioned in the lens evaluation compartment so that each of the frame-like holding means can be rotated into parallel alignment with the opening provided in the front member of the lens evaluation compartment.

The interior dividing panel of the box-like casing is positioned between the left and right side panels of the casing so that two equally-sized, vertically extending compartments having a rear wall are formed in the casing. The interior dividing panel further extends into the lens evaluation compartment and creates two equally-sized lens evaluation subcompartments that adjoin the vertically extending casing compartments behind them. With the lens evaluation subcompartments and casing compartments being so configured, the rear wall of each casing compartment will be viewable from the adjoined subcompartments. On the rear wall of each casing compartment, there are displayed a plurality of written characters, designs and/or symbols that enable a user of the apparatus of the present invention to select an optical lens.

The viewing means attachable to the apparatus is an eye mask assembly that includes a peripheral enclosure and a viewing frame which is capable of receiving, but does not contain, an optical lens, i.e., the viewing frame is devoid of an optical lens or any barrier material during the lens selection process. The viewing frame is secured to the peripheral enclosure and is provided with a means for releasably and slidably attaching the viewing frame/peripheral enclosure assembly to the top and bottom edges of the rectangular opening of the front member of the lens evaluation compartment. Being so attached, the eye mask assembly can be moved laterally in the rectangular opening and thereby permit a user of the mask to alternately look at the written characters, designs and/or symbols on each rear wall of the left and right casing compartments through each of the slide-like plates aligned with the rectangular opening. A user of the apparatus of the present invention may evaluate all optical lenses to find the most suitable of them by rotating each lens into alignment with the rectangular opening and viewing the rear wall of the casing compartment and then selecting the desired lens for insertion into a eye mask from any one of a number of lens storage compartments provided on the front panel of the apparatus.

In the preferred embodiment of the present invention, the optical lenses included on the rotating drum member are magnifying lenses which are differ incrementally in their magnifying lens power. While any range of lens powers may be included in the apparatus, the present invention has a range having a lower lens power of +0.75 diopters and an upper power of +2.50 diopters.

In view of the foregoing, it will be evident that an object of the present invention is to provide a new and unique optical lens selection apparatus for outfitting a protective eye mask, the selection apparatus being highly portable and usable at or near the point of mask use.

It is also an object of the present invention to provide a lens selection apparatus that can be easily operated by the individual mask wearer.

It is a further object of the present invention to provide a lens selection apparatus having a supply of lenses that are immediately usable by the individual mask wearer.

These and other objects of the present invention will be apparent in the following detailed description, viewed in conjunction with the accompanying drawings.

DESCRIPTION OF THE PREFERRED EMBODIMENT

Figure 1:
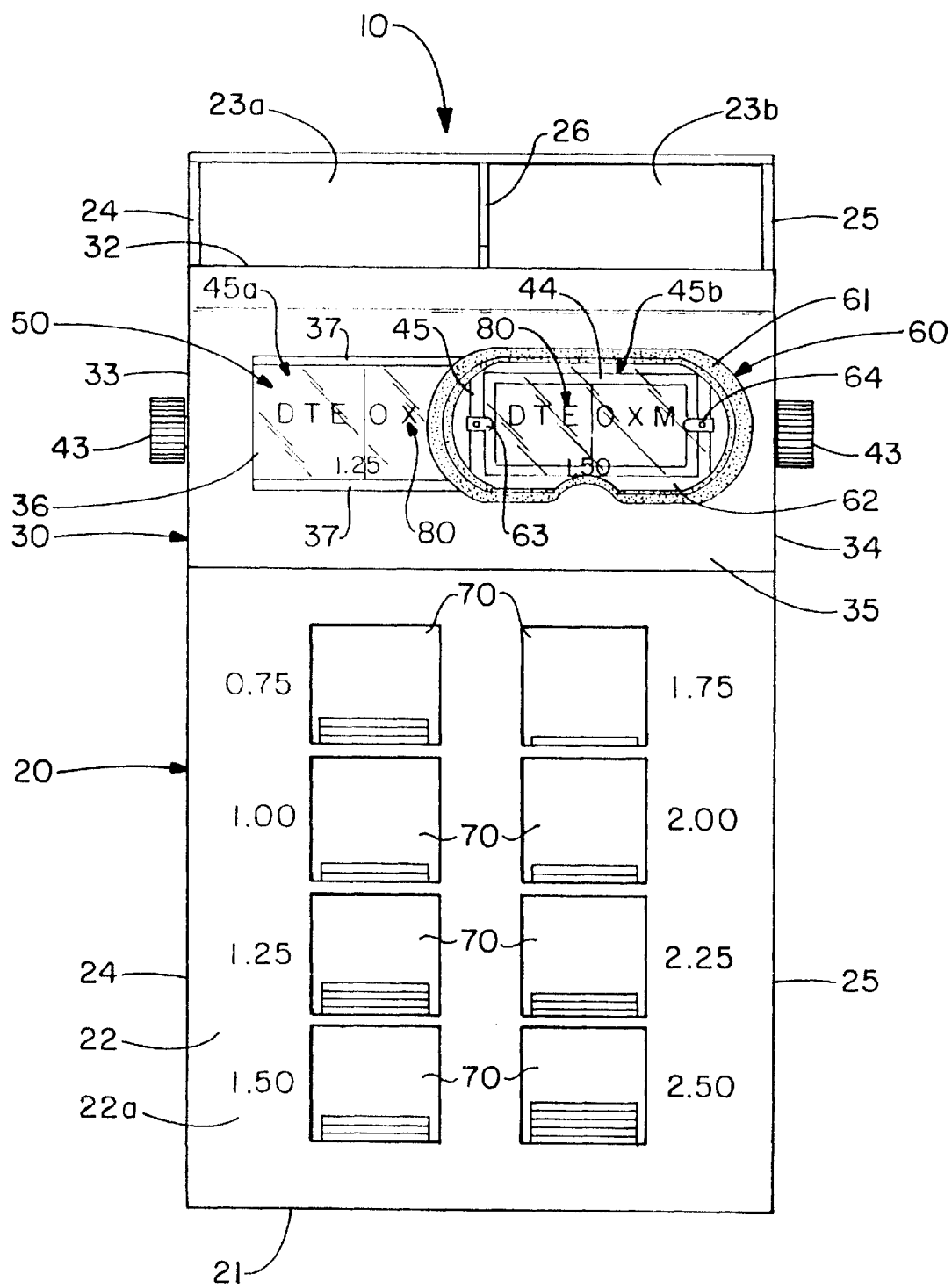
FIG. 1 is a front view of the apparatus of the present invention.
Figure 2:
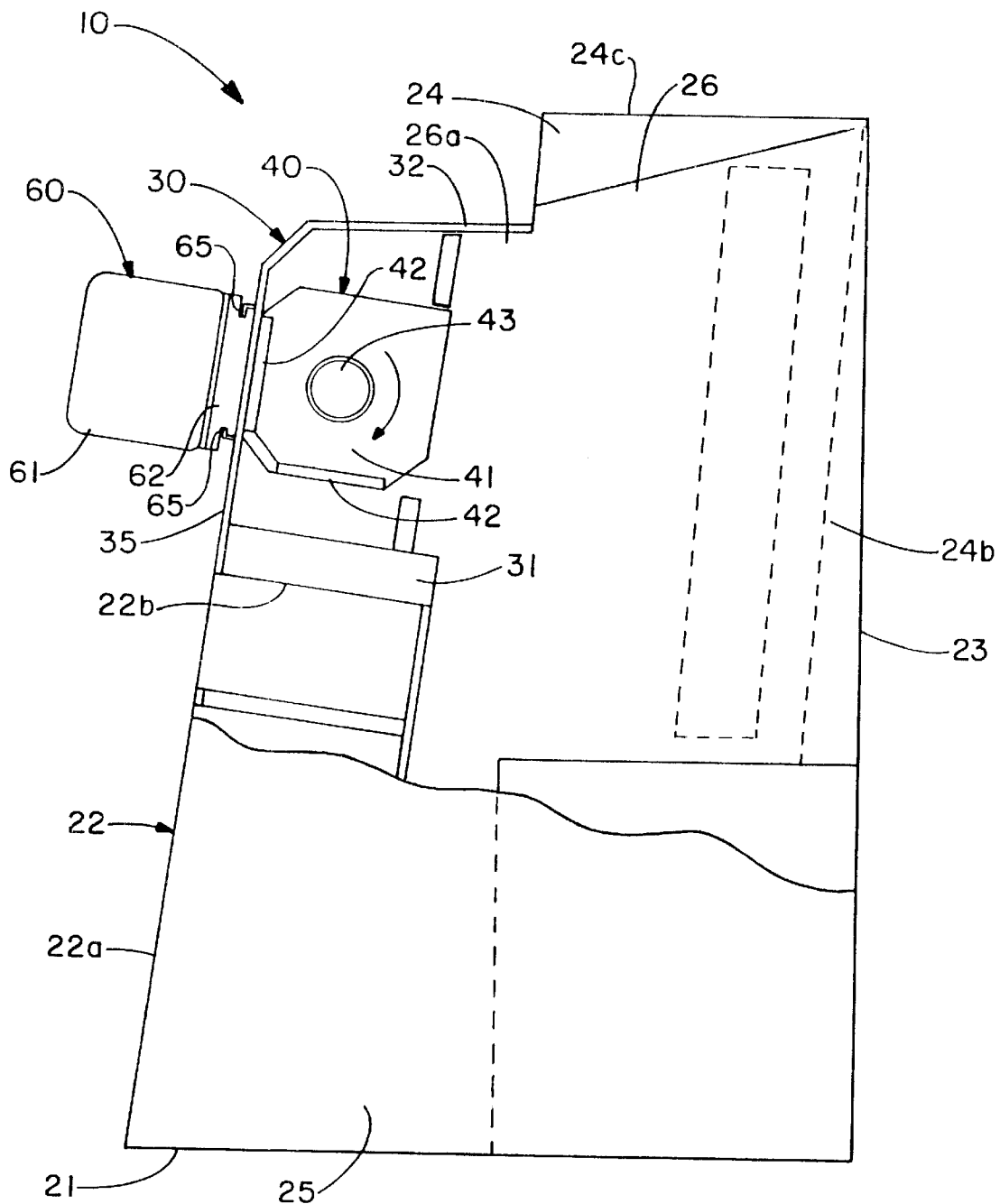
FIG. 2 is a partially cut away side view of the apparatus of the present invention.

An optical lens selection apparatus in accordance with a preferred embodiment of the present invention is indicated generally in FIG. 1 by the reference numeral 10. The apparatus 10 is fundamentally comprised of a box-like casing 20, a lens evaluation compartment 30 fixed to the casing 20, a drum member 40 situated within and movably attached to the lens evaluation compartment 30, a plurality of slide-like plates 50 fixed to the sides of the drum member 40 and a viewing means 60 that is releasably attachable to the lens evaluation compartment 30 for use with the drum member 40 with the plurality of slide-like plates 50.

Figure 3A:
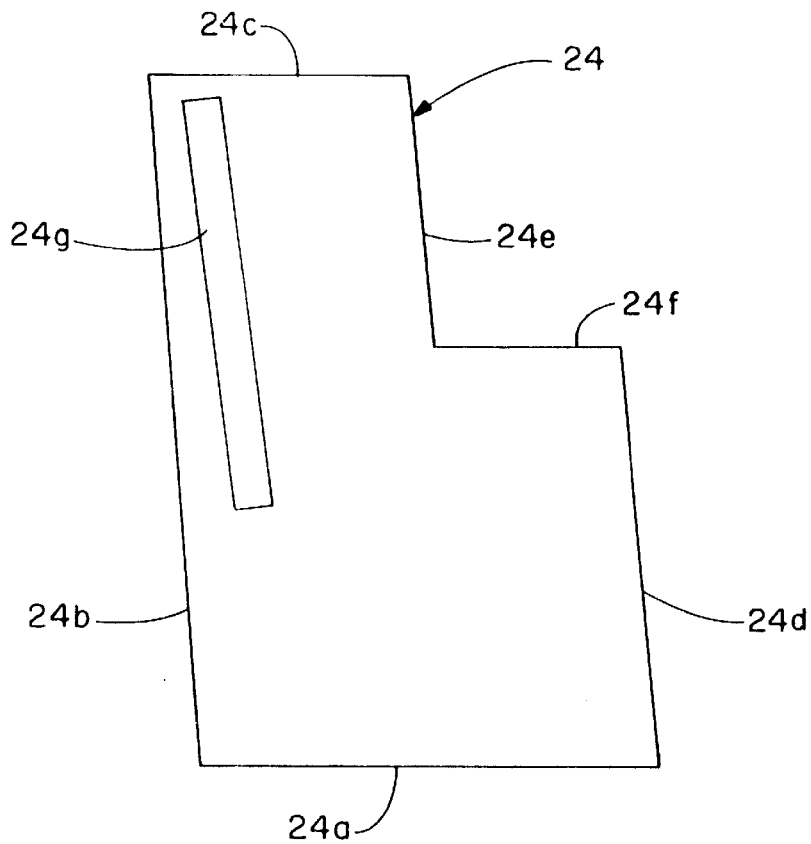
FIG. 3A is a side view of a left side panel of the apparatus of the present invention.
Figure 3B:
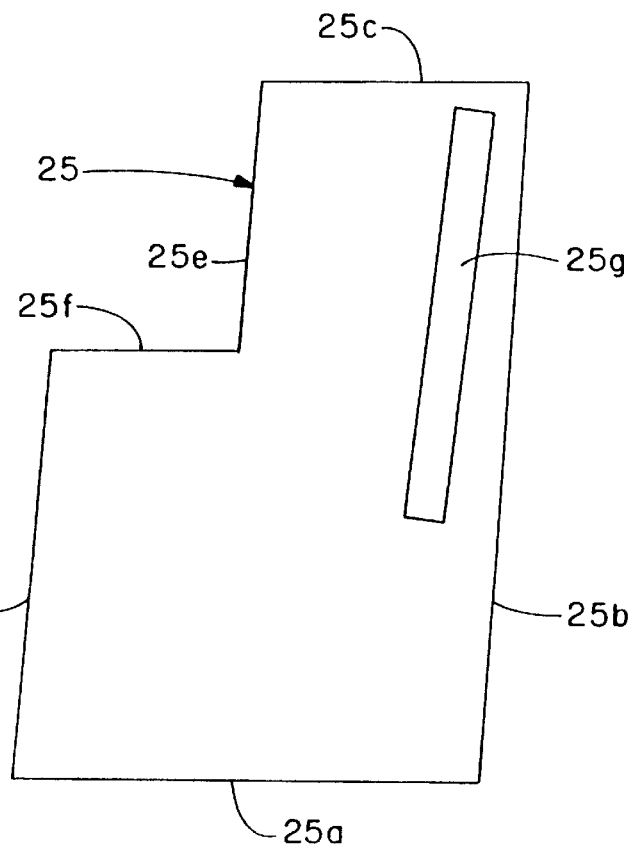
FIG. 3B is a side view of a right side panel of the apparatus of the present invention.

The box-like casing 20 includes a horizontal base 21, a front panel 22, a rear panel 23, a left side panel 24, a right side panel 25 and an interior dividing panel 26. The front panel 22, the left and right side panels 24 and 25 along with the interior dividing panel 26 extend upwardly from the horizontal base 21, and the interior dividing panel 26 further extends inwardly from the rear panel 23. The rear panel 23, which in the preferred embodiment does not fully extend vertically downward to and make contact with the horizontal base 21, is supported on its ends by the left and right side panels 24 and 25 and in its central region by the interior dividing panel 26. As may be clearly seen by reference to FIGS. 3A and 3B, the left and the right side panels 24 and 25 each have a six-sided polygon shape including: a bottom edge 24a, 25a; a rear edge 24b, 25b; a top edge 24c, 25c; a front edge 24d, 25d; a first intermediate edge 24e, 25e and a second intermediate edge 24f, 25f. The first intermediate edges 24e and 25e extend downwardly from the top edges 24c and 25c and intersect with the second intermediate edges 24f and 25f, which respectively extend rearwardly from the front edges 24d and 25d. Such arrangement of the first intermediate edges 24e and 24f and the second intermediate edges 24f and 25f serves to define a generally rectangular open area in the upper front quadrant of each of the left and right side panels 24 and 25. Each of the left and right side panels 24 and 25 are provided vertically extending, rectangular openings 24g and 25g, which are placed generally in the upper portion and toward the rear of the panels 24 and 25. Openings 24g and 25g operate to permit light to enter the interior of the casing 20. The front panel 22 of the casing 20 includes a vertically extending, lower portion 22a and a generally horizontally extending upper portion 22b. The front panel lower portion 22a is fixed at its bottom edge with the front edge of the horizontal base 21 and extends upwardly between the front edges of the left and right side panels 24 and 25. The upper portion 22b extends rearwardly from the top of the lower portion 22a and laterally between the second intermediate edges of the left and right side panels 24 and 25, and thus forms a horizontal shelf between the panels 24 and 25 the purpose of which will be explained hereinbelow. In the preferred embodiment, the horizontal base 21, the front panel 22, the rear panel 23 the left and right side panels 24 and 25, and the interior dividing panel will be produced from an easily cut and assembled, light-weight, sturdy paper board substance. It will be understood, however, that alternate embodiments of the present invention can include such components being made of any sturdy metallic or nonmetallic materials, such as sheet metal, ply wood or plastic.

The lens evaluation compartment 30 is an elongated, open-backed chamber defined by a bottom member 31, a top member 32, a left side member 33, a right side member 34 and a front member 35. As in the case of the casing 20, the listed components of the compartment 30 will preferably be fabricated of a sturdy paper board substance, with metallic and non-metallic materials being alternatives. Dimensionally, the lens evaluation compartment 30 has a length, height and depth that corresponds generally to the length of the horizontal shelf created by upper portion 22b of the front panel 22, length of each of the first intermediate edges 24e and 25e and the length of each of the second intermediate edges 24f and 25f of the left and right side panels 24 and 25. Being so dimensioned, the lens evaluation compartment 30 fits within the open area defined by intermediate edges 24e and 24f and 25e and 25f and the bottom member 31 of the compartment 30 can be securely fixed to the horizontal shelf (upper portion 22b) by any of a number of known means. The front member 35 of the lens evaluation compartment is provided with a rectangular opening 36 that extends horizontally across much of the width of the front member 35. The opening 36 permits a view of the rear panel 23 of the casing 20. A pair of channel-like strips 37 are provided for the opening 36. One of the strips 37 runs along the length of the top edge of the opening 36 and the other of the strips 37 runs along the bottom edge of the opening 36. In the preferred embodiment, the strips 37 are fabricated from extruded plastic; however, the strips 37 may be produced from other known materials such as metal or nylon to name a few.

The drum member 40 is hollow in its interior and resembles a portion of a multi-faceted prism. The drum member 40 is comprised of a pair of parallel-spaced drum end members 41 and a plurality of rectangular drum side members 42 that are fixed to and extend between the drum end members 41. Each of the drum end members 41 have a plurality of peripheral edges and each of the drum side members 42 are fixed at their opposing ends to one peripheral edge of each of the drum end members 41. Each drum side member 42 is adjoined laterally by at least one of the other drum side members so that a generally continuous, side-by-side arrangement of the drum side members 42 about the end members 41 is the result. Such arrangement of the drum side members 42 generally encloses half of the periphery of each of the drum side members 41. Each of the drum end members 41 is provided with a centrally situated drum end aperture through each of which apertures passes a rotatable fastening means such as a threaded bolt or screw having a nut that secures the bolt or screw to the drum side member 41. Each of the rotatable fastening means extends outwardly from each of the drum side members toward and through an orifice provided in each of the left and right side members 33 and 34 of the lens evaluation compartment 30. A knob-like rotating means 43 is threadably attached to the outer end of each of the rotatable fastening means. The knob-like rotating means 43 permit a user of the apparatus 10 to turn the drum 40 within the lens evaluation compartment 30.

Each side members 42 of the drum 40 includes a frame-like holder 44 that is transversely separated by a divider 45 into left and right holder portions 45a and 45b, each of which holder portions are of substantially equal areas. The frame-like holder 44 is dimensionally the same with respect to its length and width as the rectangular opening 36 in the front member 35 of the lens evaluation compartment 30. Each of the left and right holder portions 45a and 45b of each frame-like holder 44 one of the slide-like plates 50. Each of the slide-like plates 50 will be transparent, impact resistant glass or high strength plastic and will further have the characteristics of an optical lens. The optical lens characteristics of each of the slide-like plates 50 will be different. In the preferred embodiment of the present invention, the slide-like plates 50 will have the characteristics of magnifying optical lenses. It is envisioned that there will be a total of eight slide-like plates 50 and a total of four frame-like holders 44, with each of the holders 44 containing two of the slide-like plates 50. It is contemplated that the magnifying lens power of each of the slide-like plates 50 will differ in increments of one-quarter diopter, with the lowest magnifying lens power being +0.75 diopters and the highest magnifying lens power being +2.50 diopters. It is further contemplated that the slide-like plates 50 will be arranged on the drum member 40 so that a first drum side member 42 will contain plates 50 with powers of +0.75 diopters and +1.00 diopters beside one another, a second drum side member 42 will contain plates 50 with powers of +1.25 diopters and 1.50 diopters beside one another, etc.

The interior dividing panel 26 of the casing 20 is vertically situated midway between the left and right side panels 24 and 25 and divides the casing 20 into a left casing compartment and a right casing compartment. The left casing compartment has a left casing rear wall 23a and the right casing compartment has a right casing rear wall 23b. Each of the rear walls 23a and 23b are provided with one or more lines of letters 80 printed or affixed thereon. The interior dividing panel 26 includes a vertically extending portion 26a that is received by and serves to partition the lens evaluation compartment 30 into a left and a right subcompartment. The left subcompartment of the lens evaluation compartment 30 openly adjoins the left casing compartment of the casing 20 so that the left rear wall 23 and the letters 80 thereon are visible from the left subcompartment. Similarly, the right subcompartment of the lens evaluation compartment 30 openly adjoins the right casing compartment of the casing 20 so that the right rear wall 23 and the letters 80 thereon are visible from the right subcompartment.

The viewing means 60 is an eye protection mask and is comprised of a peripheral enclosure 61 that is molded to snugly rest against the forehead, temples and nose area of a user of the apparatus 10 and thus enclose the user's eyes from regions above, below and to the sides of the viewing means 60. The viewing means is further comprised of a rectangularly shaped, frame-like viewing member 62 that is securely attached to the peripheral enclosure 61 at a front opening thereof. While the viewing member 62 is provided with means 63 and 64 to hold an optical lens or a barrier material, it is devoid of any such obstructions during the lens selection process. The frame-like viewing member 62 is provided with a laterally running, outwardly projecting channel 65 on the top and bottom edges of the viewing member 62. The channels 65 function to interlock with the channel-like strips provided on the top and bottom edges of the opening 36 and thus allow the viewing means to be freely slid from one side of the opening 36 to the other side at the will of the user of the apparatus 10.

The drum member 40 is situated in the lens evaluation compartment 30 so that when the apparatus 10 is in use each side member 42 of the drum member 40 can by use of the rotating knobs 43 be brought close to and in parallel alignment with rectangular opening 36 of the lens evaluation compartment 30. The user of the apparatus 10 may evaluate all of the optical lenses contained in the slide-like plates 50 to find the most suitable of them by rotating each side member 42 containing two of the slide-like plates 50 held in the frame-like holders 44 into alignment with the rectangular opening 36 and by viewing through the plates 50 the letters 80 provided on the rear walls 23a and 23b and then immediately selecting the desired lens for insertion into a eye mask 60 from any one of a number of lens storage compartments 70 provided in the lower portion 22a of the front panel 22 of the casing 20.

While the above described preferred embodiment of the present invention disclosed the use of eight slide like plates 50 it should be understood that the present invention is not intended to be limited to such number of plates 50; rather the invention is intended to include any practical number whether such practical number may be greater or fewer than eight. Moreover, it should be understood that the plates 50 may be subdivided into two optical lenses and that the optical characteristics of such lenses may be other that magnifying characteristics. With regard to the letters 80 provided on the rear walls 23a and 23b, it should also be understood that rear walls 23a and 23b may just as readily display words, numerals, symbols, designs, photographs, drawings, graphical representations and the like, and it is intended that any or all of such wall displays whether individually or in combination with the others are within the scope of the invention.

While the preferred embodiment of the invention has been described above, it will be recognized and understood that various modifications may be made therein and the appended claims are intended to cover all such modifications which may fall within the spirit and scope of the invention.

What is claimed is:

1. An apparatus for selection of an optical lens, comprising:

a box-like casing having a horizontal base, a front panel, a rear panel, a left side panel, a right side panel and an interior dividing, panel, said front, said left side and said right side panels along with said interior dividing panel extending upwardly from said horizontal base, and said interior dividing panel further extending inwardly from and, along with said left side panel and said right side panel, supporting said rear panel;

a lens evaluation compartment fixed to said casing;

a drum member situated within and movably attached to said lens evaluation compartment;

a plurality of slide-like plates, each of said slide-like plates being provided with an optical lens, said plurality of slide-like plates being fixed to said drum member;

a viewing means releasably attachable to said lens evaluation compartment for use with said drum member and said plurality of optical lenses fixed thereto;

wherein said left side panel and said right side panel of said box-like casing each have a polygon shape, said shape having six line segments representing a bottom edge, a rear edge, a top edge, a front edge, a first intermediate edge and a second intermediate edge, said first intermediate edge intersecting with and extending downwardly from said top edge and said second intermediate edge intersecting with and extending rearwardly from said front edge, said first intermediate edge and said second intermediate edge further intersecting one another to define a generally rectangular open region in the upper, front quadrant of each of said left side and said right side panels.

2. An apparatus as claimed in claim 1, wherein said front panel of said box-like casing includes a front panel lower portion and a front panel upper portion, said front panel lower portion extending upwardly from said horizontal base panel and laterally between said front edge of each of said left side and said right side panels, and said front panel upper portion extending rearwardly from said front panel lower portion and laterally between said second intermediate edge of each of said left side and said right side panels, said front panel upper portion thus forming a horizontal shelf member extending between said left side and said right side panels.

3. An apparatus as claimed in claim 2, wherein said lens evaluation compartment is an elongated, open-backed enclosure defined by a bottom member, a top member, a left side member, a right side member and a front member, said enclosure dimensionally having a length, a height and a depth that permits said bottom member of said enclosure to be received by and fixed to said horizontal shelf member formed by said front panel upper portion of said box-like casing.

4. An apparatus as claimed in claim 3, wherein said front member of said elongated, open backed enclosure is provided with a rectangular opening extending lengthwise in said front member.

5. An apparatus as claimed in claim 4, wherein said drum member is hollow, has a shape resembling a portion of a multi-faceted prism and includes two parallel-spaced drum end members, each having a plurality of edges, and a plurality of drum side members fixed to and extending between said drum end members.

6. An apparatus as claimed in claim 5, wherein each of said drum end members is provided with a drum end aperture, said drum end aperture receiving a rotatable fastening means that extends through said drum end aperture and outwardly from each of said drum end members.

7. An apparatus as claimed in claim 6, wherein said left side member and said right side member of said lens evaluation compartment are each provided with an orifice, said orifice receiving one of said rotatable fastening means extending through said drum end.

8. An apparatus as claimed in claim 6, wherein said drum member further includes a pair of knob-like rotating means, each of said knob-like rotating means being fixed to the outside end of each of said rotatable fastening means and being used to turn said drum member in said lens evaluation compartment.

9. An apparatus as claimed in claim 8, wherein each of said drum side members is comprised of a frame-like holding means, said frame-like holding means being transversely separated by a dividing member into a left holding means portion and a right holding means portion, and said frame-like holding means further being dimensionally the same, with respect to overall length and height, as said rectangular opening in said front member of said lens evaluation compartment.

10. An apparatus as claimed in claim 9, wherein said left holding means portion and said right holding means portion each contain one of said slide-like plates provided with said optical lens.

11. An apparatus as claimed in claim 10, wherein said optical lens provided in each of said slide-like plates has a lens power, said lens power being incrementally different for each of said slide-like plates fixed to said drum member.

12. An apparatus as claimed in claim 11, wherein said lens power of each of said slide-like plates is a magnifying lens power and said optical lens in each of said slide-like plates is a magnifying lens.

13. An apparatus as claimed in claim 12, wherein said magnifying lens power of each of said slide-like plates is in a range having a lower power of +0.75 diopters and an upper of +2.50 diopters.

14. An apparatus as claimed in claim 9, wherein said drum member is situated in said lens evaluation compartment so that each of said frame-like holding means can, by use of said knob-like rotating means, be brought proximate to and into parallel alignment with said rectangular opening of said front member of said lens evaluation compartment.

15. An apparatus as claimed in claim 14, wherein said interior dividing panel of said box-like casing is situated equidistantly between said left side panel and said right side panel to define in said box-like casing a left side casing compartment having a left side casing compartment rear wall and a right side casing compartment having a right side casing compartment rear wall, and said interior dividing panel includes a vertical extending portion that is received by and serves to partition said lens evaluation compartment into a left side lens evaluation sub-compartment and a right side lens evaluation sub-compartment, said left side lens evaluation sub-compartment openly adjoining said left side casing compartment so that said left side casing compartment rear wall is visible from said left side lens evaluation sub-compartment and said right side lens evaluation sub-compartment openly adjoining said right side casing compartment so that said right side casing compartment rear wall is visible from said right side lens evaluation sub-compartment.

16. An apparatus as claimed in claim 15, wherein said left side casing compartment rear wall and said right side casing compartment rear wall are provided therein with any one of a group consisting of letters, numerals, symbols, designs, photographs, drawings and graphical representations.

17. An apparatus as claimed in claim 15, wherein said viewing means comprises a protective covering for a pair of eyes.

18. An apparatus as claimed in claim 17, wherein said protective covering includes a peripheral enclosure member and an unobstructed frame-like viewing member, said viewing member being securely attached to said peripheral enclosure member at a front opening provided in said enclosure member.

19. An apparatus as claimed in claim 18, wherein said viewing member includes a means for releasably attaching said protective covering to said rectangular opening in said front member of said lens evaluation compartment and for allowing said protective covering to be slidably moved laterally along the top and bottom edges of said rectangular opening and to thereby permit a user of said protective covering to alternately look at said left side casing compartment rear wall and said right side casing compartment rear wall through said rectangular opening and through each of said slide-like plates aligned with said rectangular opening.

20. An apparatus as claimed in claim 18, wherein said front panel lower portion of said front panel of said box-like casing has a plurality of pigeonhole-like recesses for holding a supply of viewing lenses from which said user of said protective covering can select a suitable viewing lens for insertion into said frame-like viewing member after said user has viewed said left side casing compartment rear wall and said right side casing compartment rear wall and has removed said protective covering from said rectangular opening in said front member of said lens evaluation compartment.

* * * * *